(12) United States Patent
Puttlitz et al.

(10) Patent No.: US 9,636,149 B2
(45) Date of Patent: *May 2, 2017

(54) PEDICLE SCREW ASSEMBLY AND DYNAMIC SPINAL STABILIZATION DEVICES INCORPORATING THE PEDICLE SCREW ASSEMBLY

(71) Applicant: Colorado State University Research Foundation, Fort Collins, CO (US)

(72) Inventors: Christian M. Puttlitz, Fort Collins, CO (US); Benjamin C. Gadomski, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/977,063

(22) Filed: Dec. 21, 2015

(65) Prior Publication Data

US 2016/0106476 A1    Apr. 21, 2016

Related U.S. Application Data

(62) Division of application No. 13/983,020, filed as application No. PCT/US2011/050358 on Sep. 2, 2011, now Pat. No. 9,226,779.

(60) Provisional application No. 61/438,719, filed on Feb. 2, 2011.

(51) Int. Cl.
   *A61B 17/70* (2006.01)
(52) U.S. Cl.
   CPC ...... *A61B 17/7038* (2013.01); *A61B 17/7032* (2013.01); *A61B 17/7055* (2013.01); *A61B 17/7067* (2013.01); *A61B 17/7071* (2013.01)

(58) Field of Classification Search
   CPC ............ A61B 17/7032; A61B 17/7034; A61B 17/7035; A61B 17/7046; A61B 17/86; A61B 17/8605
   See application file for complete search history.

(56) References Cited

U.S. PATENT DOCUMENTS

| 7,951,171 B2 * | 5/2011 | Woods | A61B 17/7037 606/264 |
| 8,945,185 B2 | 2/2015 | Puttlitz et al. | |
| 9,226,779 B2 | 1/2016 | Puttlitz et al. | |
| 2005/0143823 A1 * | 6/2005 | Boyd | A61B 17/7032 623/17.16 |
| 2005/0154390 A1 * | 7/2005 | Biedermann | A61B 17/7035 128/898 |

(Continued)

OTHER PUBLICATIONS

Final Office Action, U.S. Appl. No. 14/577,906, filed Jan. 25, 2016.

(Continued)

*Primary Examiner* — Eduardo C Robert
*Assistant Examiner* — Julianna N Harvey
(74) *Attorney, Agent, or Firm* — Polsinelli PC

(57) ABSTRACT

A dynamic spinal stabilization device for the treatment of high-grade spinal disorders is disclosed herein. The dynamic spinal stabilization device includes two or more screw assemblies, each of which include a pedicle screw and a head socket containing a curved internal track that limits the range of motion and center of rotation of the spinal segments stabilized using the device to the physiological levels of a nondegraded spinal segment.

21 Claims, 17 Drawing Sheets

(56) References Cited

U.S. PATENT DOCUMENTS

| | | | |
|---|---|---|---|
| 2005/0187548 A1* | 8/2005 | Butler | A61B 17/7032 606/278 |
| 2007/0270813 A1* | 11/2007 | Garamszegi | A61B 17/7032 606/278 |
| 2009/0210015 A1* | 8/2009 | Cermak | A61B 17/7037 606/305 |
| 2011/0202094 A1* | 8/2011 | Pereira | A61B 17/7037 606/305 |
| 2015/0105825 A1 | 4/2015 | Puttlitz et al. | |

OTHER PUBLICATIONS

Response to Final Office Action, U.S. Appl. No. 14/577,906, filed Apr. 7, 2016.
Response to Non-Final Office Action, U.S. Appl. No. 14/577,906, filed Nov. 2, 2015.

* cited by examiner

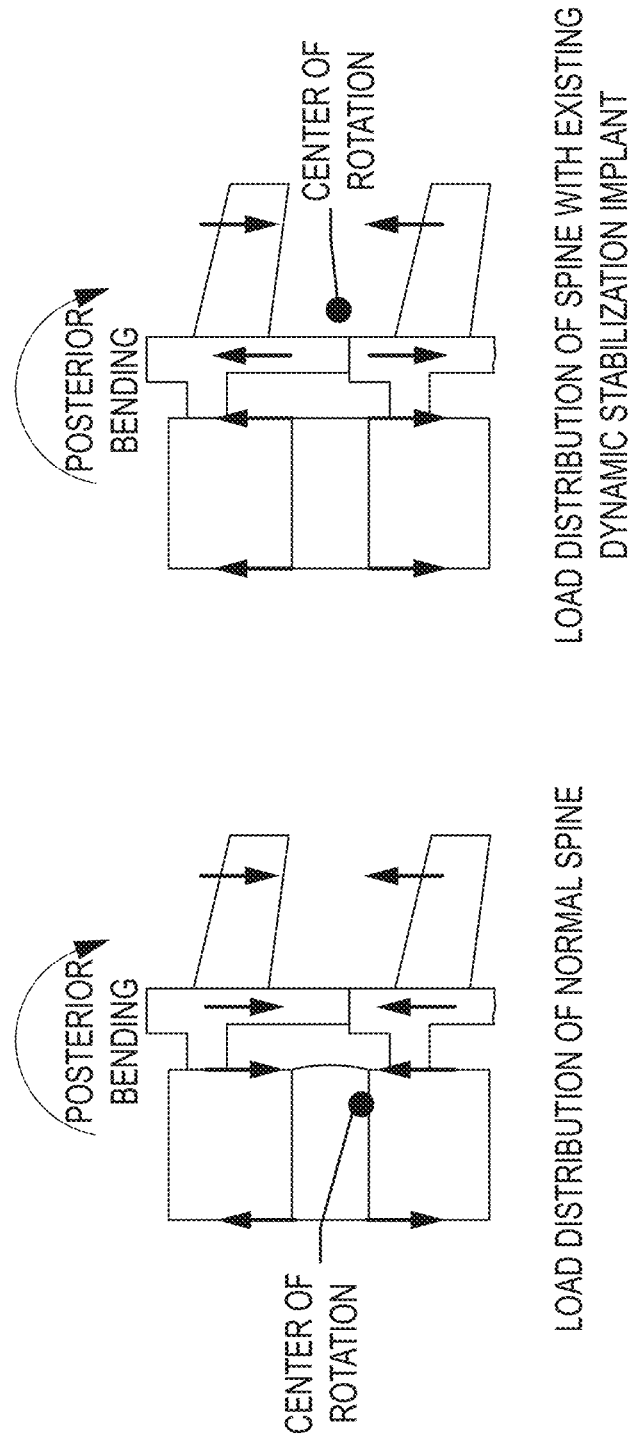

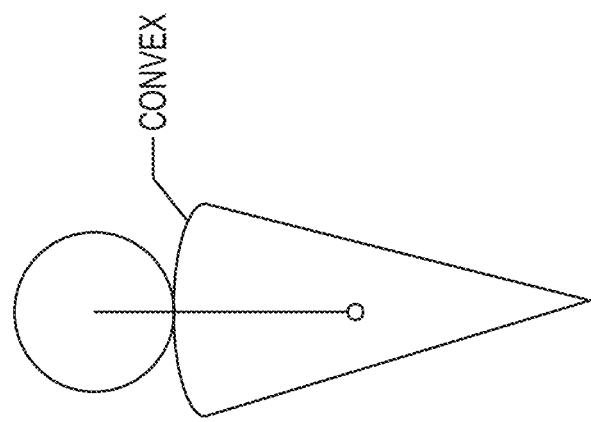
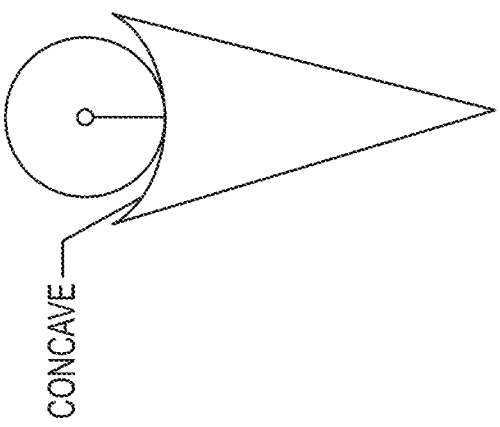
FIG. 2B
FIG. 2A

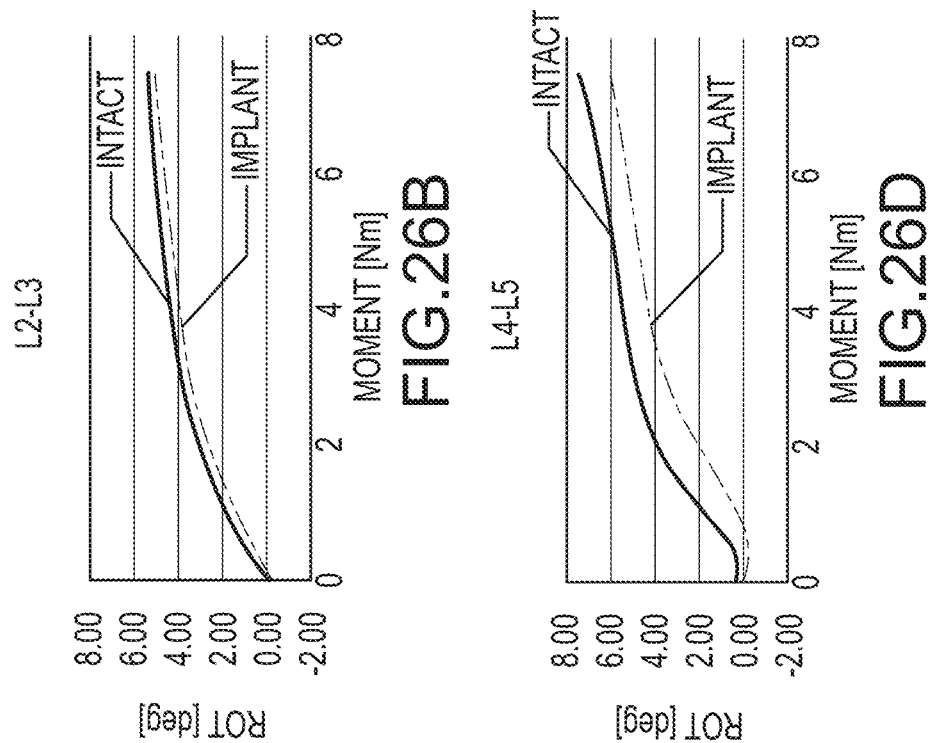
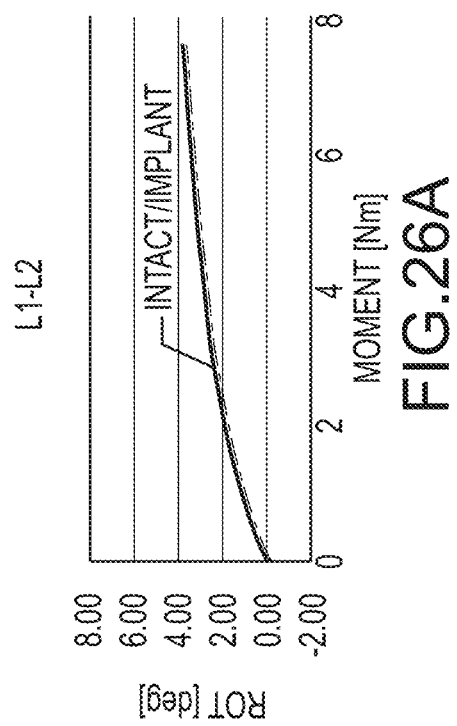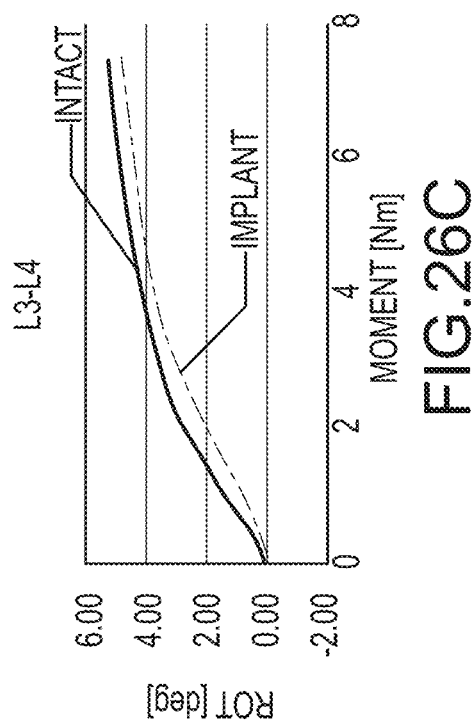

PEDICLE SCREW ASSEMBLY AND DYNAMIC SPINAL STABILIZATION DEVICES INCORPORATING THE PEDICLE SCREW ASSEMBLY

CROSS REFERENCE TO RELATED APPLICATIONS

This application is a divisional of U.S. application Ser. No. 13/983,020 filed Jul. 31, 2013, which application is a national stage entry of Patent Cooperation Treaty (PCT) No. PCT/US2011/050358 filed Sep. 2, 2011, which application claims the benefit under 35 U.S.C. §119(e) of: U.S. Provisional Application 61/438,719, filed Feb. 2, 2011 and titled "Dynamic Stabilization Device for the Manipulation of the Axis of Rotation of the Lumbar Spine and Correction of the Center of Rotation in the Lumbar Spine". The contents of the above-mentioned patent applications are hereby incorporated by reference in their entireties.

The present application is related to PCT patent application No. PCT/US2011/050370, which is entitled "Interspinous Spacer Devices For Dynamic Stabilization Of Degraded Spinal Segments", filed Sep. 2, 2011, and incorporated by reference in its entirety into the present application.

FIELD OF THE INVENTION

The present invention relates to devices for the treatment of high-grade spinal disorders. More specifically, the present invention relates to dynamic spinal stabilization devices.

BACKGROUND OF THE INVENTION

Posterolateral fusion is the standard procedure for treating high grade spinal disorders such as spinal stenosis as well as spondylolisthesis. Despite the wide-spread use of posterolateral fusion as a surgical approach for correcting back pain, numerous problems have been associated with its use. Spinal fusion recipients may be at risk for developing Adjacent Segment Disease (ASD), a condition in which the motion segments adjacent to the fused vertebral segments experience higher rates of degeneration deterioration due to an increase in vertebral loading, higher intradiscal pressures, increased range of motion, and increased facet motion.

Dynamic spinal stabilization has recently emerged as an alternative procedure to treat many degenerative spinal disorders. Existing dynamic stabilization devices restore stability to an injured spine while simultaneously allowing a restricted range of motion. These devices are designed to preserve the integrity of adjacent segments by minimizing the transfer of segment motion and facet joint forces between the stabilized spinal segment and the adjacent spinal segments.

Existing dynamic spine stabilization devices incorporate selectively flexible elements such as flexible cords and intravertebral spacers, or flexible spring rods in order to allow a constrained range of motion to the stabilized spinal segment. To date, no existing dynamic spine stabilization device constrains the rotation of the stabilized segments to a center of rotation that is coincident with a physiological center of rotation. Physiologically representative loading of a spinal segment that is stabilized using a dynamic stabilization device is unlikely to occur unless the rotational motion of the spinal segment passes through the spine's natural center of rotation. The imposition of a non-physiological center of rotation location by existing dynamic stabilization devices may result in alterations to the physiological pattern of tissue stresses and may further increase the likelihood of hardware failure. These altered tissue stresses and non-physiological motion patterns may also be induced in adjacent motion segments, increasing the likelihood of long-term complications, such as ASD, associated with existing stabilization procedures.

There is a need in the art for a dynamic spinal stabilization system that not only allows limited motion of injured or deteriorated vertebral segments, but that constrains that motion to a range that is consistent with the range of motion of the corresponding normal healthy vertebrae. In particular, a need exists for an existing dynamic spine stabilization system in which the vertebrae are constrained to rotate about an axis that is consistent with a normal healthy spine.

BRIEF SUMMARY OF THE INVENTION

In one embodiment, a screw assembly for use in a dynamic spinal stabilization device is disclosed herein. The screw assembly includes a cylindrical head socket and a pedicle screw. The head socket includes a slot extending diametrically across a central portion of a lower face of the head socket. The slot opens into an internal curved groove defined within the cylindrical head socket. The pedicle screw includes a screw head that is retained within the internal curved groove and a screw neck extending downward from the screw head through the slot. The screw head freely slides along the internal curved groove along a range of movement that is limited by a length of the slot. Further, the center of rotation of the pedicle screw is situated at a distance downward from the screw head that is equal to a radius of curvature of the internal curved groove.

In another embodiment, a screw assembly for use in a dynamic spinal stabilization device is disclosed herein. The screw assembly includes a cylindrical head socket that includes a lower face containing a slot extending diametrically across a central portion of the lower face. The slot also extends upward between the lower face and a curved lower cavity surface of an upper cavity. The screw assembly also includes a snap-in lock that includes an exposed upper surface and a curved lower lock surface. The snap-in lock is locked into place over the curved lower cavity surface, forming an internal curved groove between the curved lower lock surface and the curved lower cavity surface. The screw assembly also includes a pedicle screw that includes a screw head retained within the curved groove and a screw neck extending downward from the screw head through the slot. The screw head freely slides along the internal curved groove along a range of movement limited by the length of the slot. A center of rotation of the pedicle screw is situated at a distance downward from the screw head that is equal to the radius of curvature of the curved groove.

In an additional embodiment, a dynamic spinal stabilization device is disclosed herein. The dynamic spinal stabilization device includes at least two screw assemblies, at least one connecting rod, and at least two threaded caps. Each of the at least two screw assemblies includes a cylindrical head socket that contains a slot extending diametrically across a central portion of a lower face of the head socket. The slot opens into an internal curved groove defined within the cylindrical head socket. Each of the at least two screw assemblies also includes a pedicle screw that includes a screw head retained within the internal curved groove and a screw neck extending downward from the screw head through the slot. Each end of the connecting rod is situated within an exposed upper groove extending diametrically across an upper face opposite to the lower face of each head socket. Each end of each connecting rod is secured between each upper face of each head socket and each threaded end cap in a force-fit attachment in which each end cap is situated within a threaded fitting formed within an uppermost portion of each exposed upper groove.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 1A and 1B are schematic drawings of the load distribution on a normal vertebral segment (FIG. 1A) and on a vertebral segment constrained to rotate about a different center of rotation by a dynamic stabilization device.

FIGS. 2A and 2B are drawings illustrating the effect of concave (FIG. 2A) versus convex (FIG. 2B) curvature of stabilization device surfaces on the location of its center of rotation.

FIGS. 26A-26D are graphs showing the relative rotation as a function of applied flexion moment estimated using finite element models during spinal flexion for an intact spine and an injured spine stabilized with a dynamic spinal stabilization implant for different levels: L1-L2 (FIG. 26A), L2L3 (FIG. 26B, L3-L4 (FIG. 26C), and L4-L5 (FIG. 26D).

Corresponding reference characters indicate corresponding elements among the views of the drawings. The headings used in the figures should not be interpreted to limit the scope of the claims.

DETAILED DESCRIPTION

Figure 3:
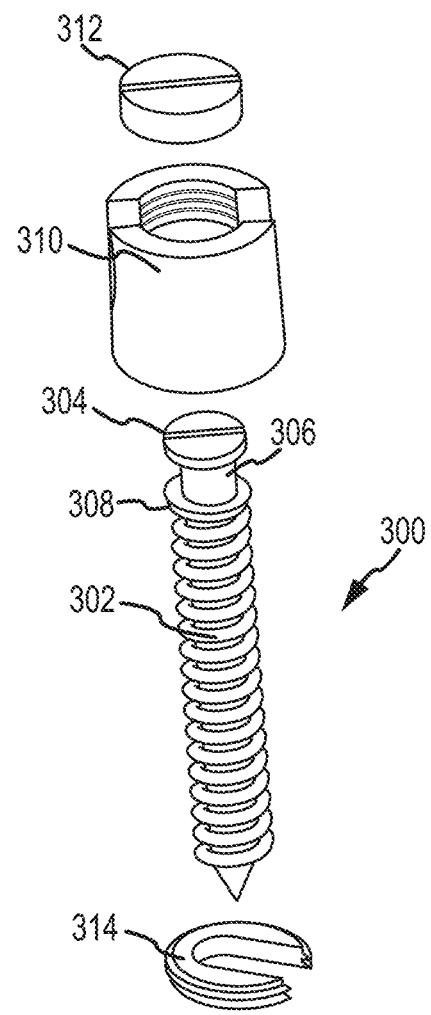
FIG. 3 is an exploded view of an embodiment of a pedicle screw assembly of a dynamic spinal stabilization device.

Pedicle screws for use in dynamic spine stabilization devices for the relief of conditions including but not limited to stenosis, discogenic pain, and spondylolisthesis in the lumbar spine are disclosed herein. The pedicle screws incorporate a novel head socket design that achieves stabilization of an injured spinal section, while preserving the center of rotation of the stabilized spinal section at a location corresponding to its natural, undegenerated location. By preserving the center of location, the devices disclosed herein preserve motion segment loading and vertebral motion of the stabilized spinal segments and adjacent spinal segments to natural, undegenerated levels. In addition, the pedicle screws are designed to accommodate treatments using multilevel dynamic spine stabilization devices.

a. Principle of Design

Embodiments of the dynamic spine stabilization devices provide enhanced structural support to compensate for degenerated spinal structures while simultaneously preserving a range of motion that is comparable to the natural motion of the undegenerated spinal segment. A critical factor governing the motion and segment loading of a stabilized spinal segment is the location of the center of rotation of the stabilized segment.

Center of rotation, as used herein, describes the spatial location of an axis of rotation about which two adjacent vertebrae rotate relative to one another in the course of an overall rotation of the spine. The overall rotation of the spine may occur as the result of any number of movements including but not limited to dorso-ventral flexion and extension, lateral bending to the left or right, axial rotation (twisting) and any combination thereof. In order to accomplish any of these overall movements, individual adjacent vertebrae rotate relative to one another in a variety of directions. In the process of these movements, loads are also transmitted between adjacent vertebrae in a characteristic pattern.

FIG. 1A is a schematic diagram illustrating the center of rotation and load distribution between two adjacent vertebrae of a healthy spine during an overall posterior extension movement. Typically, the center of rotation is located somewhere within the anterior portion of the spine as shown in FIG. 1A. This center of rotation further results in tensile loading in those regions of the vertebra anterior to the center of rotation and compressive loads in those regions posterior to the center of rotation.

Existing dynamic spinal stabilization devices typically include a hinge or other rotating element in the region posterior to the vertebral disks due to the constraints imposed by the task of implanting structurally reinforcing devices onto posterior spinal structures using existing surgical procedures. As a result, the center of rotation of a spinal segment stabilized using existing dynamic spinal stabilization devices typically have centers of rotation that are shifted significantly in a posterior direction, as illustrated in FIG. 1B. In addition, the loading pattern between the two adjacent vertebrae is altered such the vertebra experience tensile loading over a significantly larger proportion of their anterior regions, and significantly less compressive loading during the posterior extension movement illustrated in FIG. 2B.

The instantaneous center of rotation (ICR) in the lumbar motion segment in the neutral posture is typically located slightly posterior of the center of the intervertebral disc in a normal spine. Although the ICR shifts in an anterior and superior direction during spinal flexion and in a posterior direction during extension, the ICR typically remains situated within the disc or within the upper aspect of the inferior vertebra. Greater variations in the location of the ICR during movement are known to appear in degenerated spines. This occurrence of the ICR outside normal physiological limits has been associated with spinal pathology.

In order to preserve the vertebral center of rotation at its natural location, embodiments of the dynamic spinal stabilization devices project the center of rotation to a location that is anterior of the device's location. This anterior projection of the center of rotation is accomplished by configuring the geometry of the device such that the rotation does not occur along an internal axis. The concept by which embodiments of the dynamic spinal stabilization devices disclosed herein project the center of rotation in an anterior direction is illustrated in FIG. 2.

FIGS. 2A and 2B illustrate a round ball that is free to roll on either a concave or a convex surface, respectively. As shown in FIG. 2A, a round ball that rolls on a concave surface will rotate around a center of rotation in the geometric center of the ball. The cup-like concave surface cradles the ball and projects the axis of rotation back into the rolling ball. However, if the same ball rolls on a convex surface as shown in FIG. 2B, the center of rotation is projected downward and away from the ball.

Embodiments of the dynamic spinal stabilization devices incorporate this concept of center of rotation projection as a basis for the device's design. By utilizing a convex surface with a specific radius, the device may be configured such that the center of rotation of the stabilized spinal segment is projected back into the anterior portion of the spine. Embodiments of the devices make use of a sliding motion for device movement rather than the conventional rotation associated with a ball and socket design typical of existing dynamic spinal stabilization devices. The anterior distance that the center of rotation is projected from embodiments of the device may be controlled by altering the radius of the convex surface inside of the device.

b. Dynamic Spinal Stabilization Devices

Embodiments of the dynamic spinal stabilization device comprise a bilateral pedicle screw system that may include at least four screw assemblies. An exploded view of an individual screw assembly 300 is illustrated in FIG. 3. Each screw assembly 300 includes a pedicle screw 302, a head socket 310, a locking ring 314, and a head cap 312. The pedicle screw 302 has a rounded head 304 that slides within a curved groove defined within the head socket 310. In addition, the pedicle screw 302 has a cylindrical neck 306 and a raised lip 308 to prevent over tightening of the pedicle screw 302 during surgery.

Any pedicle screw design known in the art may be used in various embodiments, so long as the screw head 304 is capable of moving smoothly through the curved groove defined within the head socket 310 with the desired range of motion. In one embodiment, the pedicle screw 302 may have a screw head 304 with a diameter of about 8 mm and a radius of curvature of about 80 mm on the head surface. In this embodiment, the pedicle screw may have an overall length of about 51.7 mm, a thread angle of about 60° and a thread pitch of about 2.25. The lip 308 may be situated about 4.0 mm below the screw head 304 in this embodiment. In another embodiment, the screw head 304 may be coated with an ultra-high molecular weight polyethylene (UHMWPE) coating for added wear resistance and decreased friction.

Figure 4:
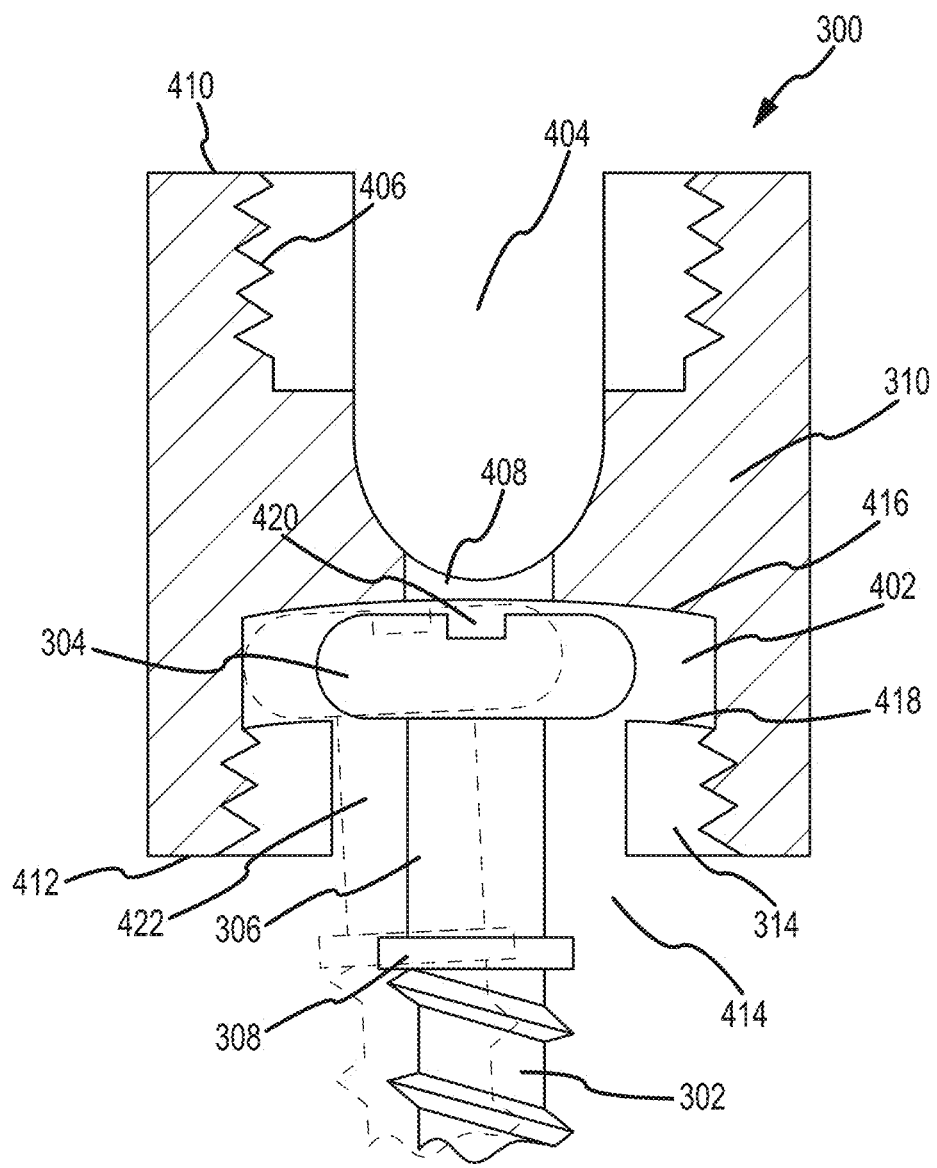
FIG. 4 is a cross-sectional view of a pedicle screw assembly.

A cross-sectional view of the screw assembly 300 is illustrated in FIG. 4. The lower face 412 of the head socket 310 contains a threaded lower cavity 414 into which the locking ring 314 may be threaded to secure the round head 304 of the pedicle screw 302 in a sliding engagement. When assembled, the upper surface 418 of the locking ring and the lower surface 416 of the head socket 310 define a curved groove 402 within which the round head 304 of the pedicle screw 302 may slide within a limited range of motion defined by the length of the slot 422, which extends diametrically across a portion of the lower face 412. The pedicle screw 302 shown in dashed lines is positioned at one extreme of the range of motion of the pedicle screw 302 in this embodiment.

The dimensions of the curved groove 402 are a critical aspect of the design of the dynamic spinal stabilization device. The curved groove 402 governs the range of motion of the spinal segment stabilized by the device. The length of the groove 402 limits the range of rotational movement of the stabilized spinal segment to within a physiological range corresponding to the movements of normal healthy vertebra. The curvature of the groove 402 projects the center of rotation of the stabilized vertebra to a location consistent with the center of rotation of corresponding normal, healthy vertebra. In one aspect, the radius of curvature of the curved groove 402 is essentially equal to the distance between the screw head 304 and the center of rotation of the stabilized vertebra. In another embodiment, the surface of the screw head 304 may be contoured to have a radius of curvature that is matched with the radius of curvature of the groove 402.

The radius of curvature of the curved groove 402 may depend on any one or more of at least several factors, including but not limited to: the dimensions of the head socket 310 and pedicle screw 302, the dimensions of the vertebra to which the screw assembly 300 is to be attached, and the desired center of rotation location. In one embodiment, the radius of curvature of the curved groove may be about 80 mm.

In an embodiment, the head socket 310 may have an overall diameter of about 16.5 mm and a height of about 15.0 mm. The overall length of the curved groove 402 within the head socket may be about 12.0 mm with a groove height of about 3.0 mm. The threads cut into the threaded lower cavity 414 of the head socket 310 and the locking ring 312 may have an M12×1 MM thread design.

The upper surface 410 of the head socket 310 contains an upper groove 404 as well as an access bore 408. A rod (not shown) may be situated within the upper groove 404 and held in a fixed position by twisting the threaded head cap 312 into the threaded cap receptacle 406. Sufficient torque may be applied to the head cap 312 so as to hold the rod in a fixed force-fit engagement. In one embodiment, the head cap 312 may have a thickness of 3.0 mm, a diameter of 10.0 mm, and the threads of the head cap 312 and threaded cap receptacle 406 may have a matched M12×1 MM thread pattern.

Figure 5:
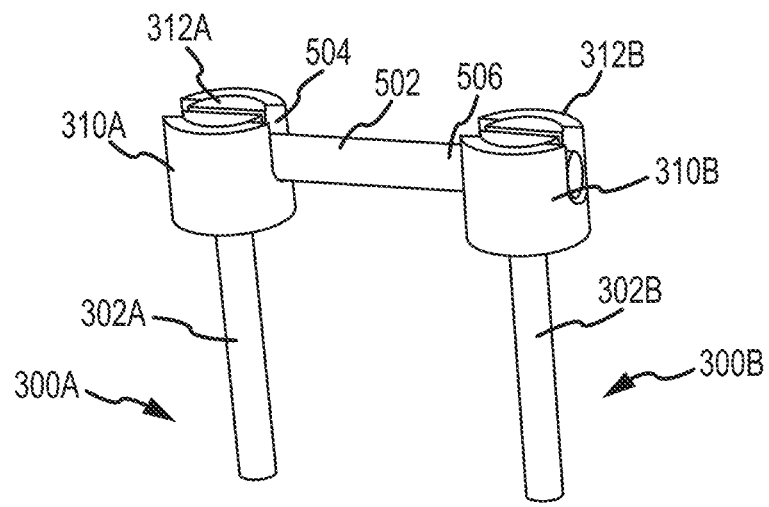
FIG. 5 is a drawing showing an assembled a dynamic stabilization device including two pedicle screw assemblies connected with a rod.

The pedicle screws 302A and 302B may be affixed into lateral processes of two adjacent vertebrae on either side of a spinal injury. FIG. 5 illustrates two screw assemblies 300A and 300B attached in a fixed manner by a rod 502. A first end 504 of the rod 502 may be held in a fixed position to the first head socket 310A by tightening the first head cap 312A. The second end 506 of the rod 502 opposite to the first end 504 may be similarly attached to a second head socket 3108 by tightening the second head cap 312B. In one embodiment, the rod 502 may be a titanium rod with a diameter of 6.35 mm (¼ inch).

In one embodiment, the dynamic spinal stabilization device comprises two pairs of pedicle screws connected in this manner, and each connected pair of pedicle screws are situated on opposite lateral sides of a spinal disorder. In another embodiment, a longer rod 502 may be used to connect three or more screw assemblies 300 in order to stabilize spinal disorders involving three or more degenerated vertebrae.

Figure 6:
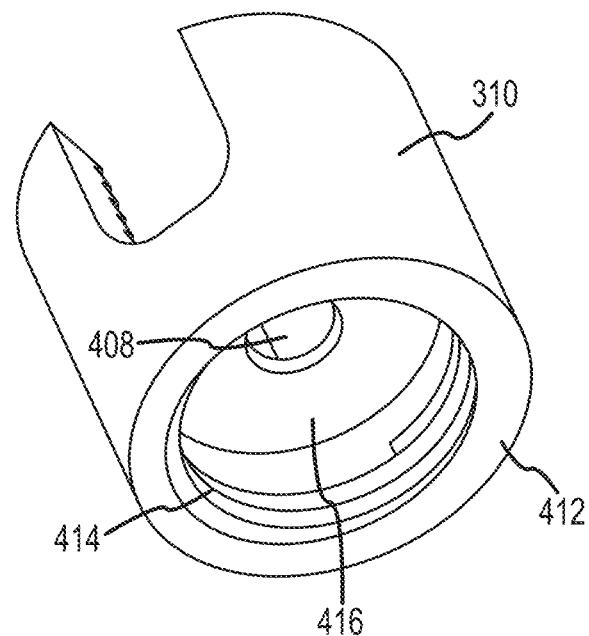
FIG. 6 is a perspective view of the lower surface of a head socket.
Figure 7:
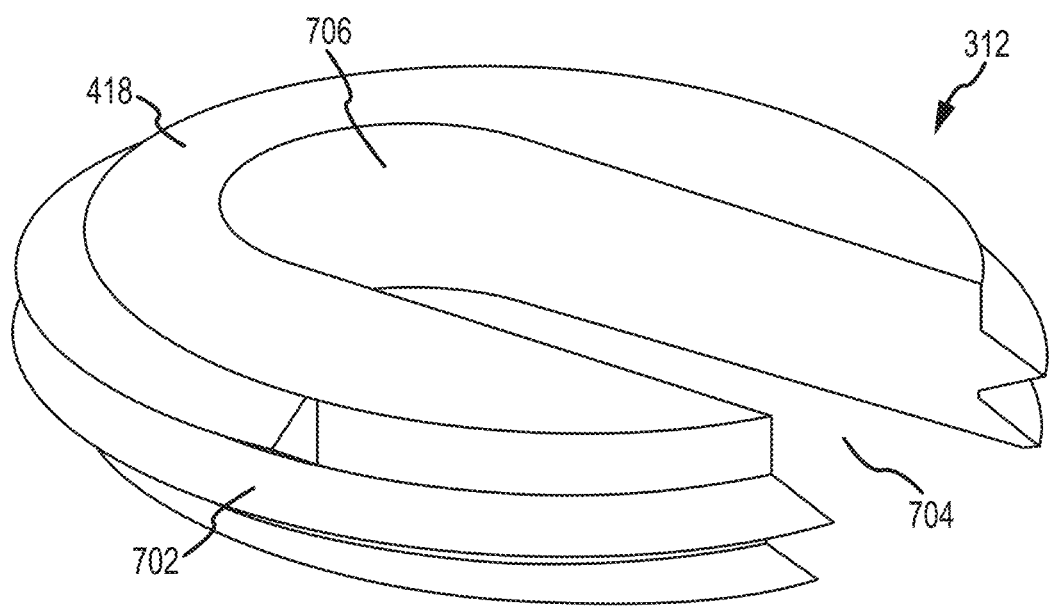
FIG. 7 is a perspective view of a locking ring.

FIG. 6 is a bottom perspective view of the head socket 310 showing the lower face 412, the access bore 408, and the threaded lower cavity 414. FIG. 7 is a top perspective view of the locking ring 312 showing the curved upper surface 418 and the threaded edge 702 designed to mate with the threads of the lower cavity 414. The locking ring 312 also contains a slot 704 with a rounded end 706 through which the neck 306 of the pedicle screw 302 protrudes. The width of the slot 704 is sized to be sufficiently wide for the neck 306 to smoothly slide along the slot 704 without significant friction or catching, but sufficiently narrow to prevent the screw head 304 from separating from the head socket 310. In one embodiment, the locking ring 312 may have an overall diameter of 12.0 mm and a slot 704 of the locking ring 312 may have a width of 5.5 mm. A radius of curvature of 80 mm may be applied to the upper surface 418 of the lock ring.

In an embodiment, the dynamic spinal stabilization device may be installed in the lumbar spinal region. In this embodiment, the device may allow no more than about 7°-10° of movement in flexion and no more than about 7°-10° of movement in extension of the stabilized vertebral segment, corresponding to a total of no more than about 14°-20° of movement for combined flexion and extension for a lumbar vertebral segment stabilized using a complete bilateral stabilization system.

Figure 8:
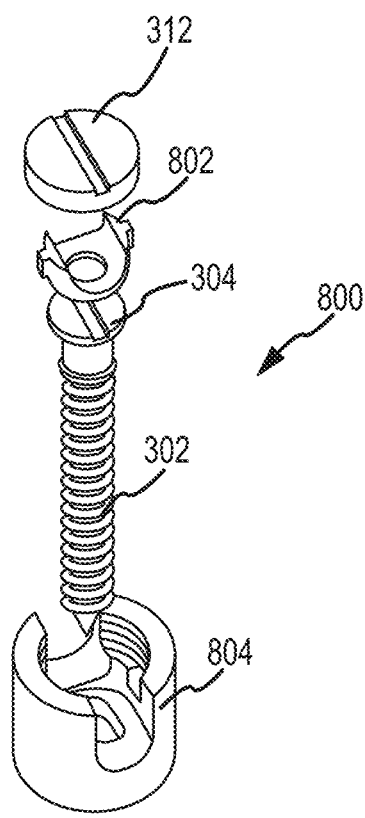
FIG. 8 is an exploded view of a screw assembly that includes a snap-in lock.
Figure 9:
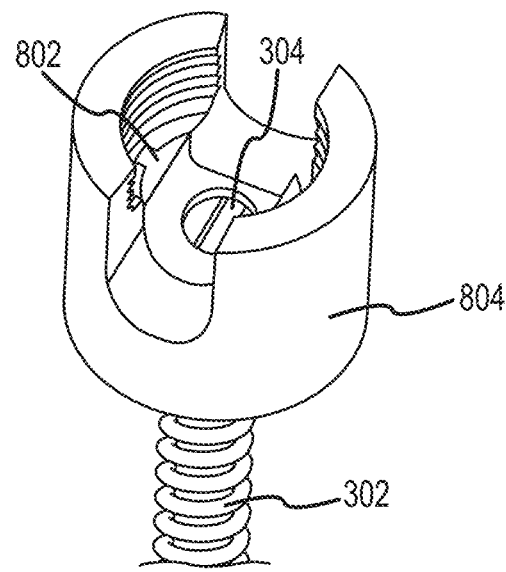
FIG. 9 is a perspective view of the upper surface of a screw assembly that includes a snap-in lock.

FIG. 8 is an exploded view of another embodiment of a screw assembly 800. This embodiment includes a pedicle screw 302 with a rounded screw head 304 and a head socket 804 with an integrated lower surface of the curved groove. The screw assembly 800 further includes a snap-in lock 802, and a cap screw 312. In this embodiment, the screw assembly 800 may be assembled by inserting the pedicle screw 302 through the head socket 804, and snapping in the lock 802 over the rounded screw head 304, as illustrated in FIG. 9. In this embodiment, the bottom portion of the head socket 804 was designed as a solid piece to improve strength where screw movement occurs. In at least one embodiment, the lock is at least one tab insertable into a correspondingly shaped indention in the upper cavity when the lock is placed in the head socket.

Figure 10:
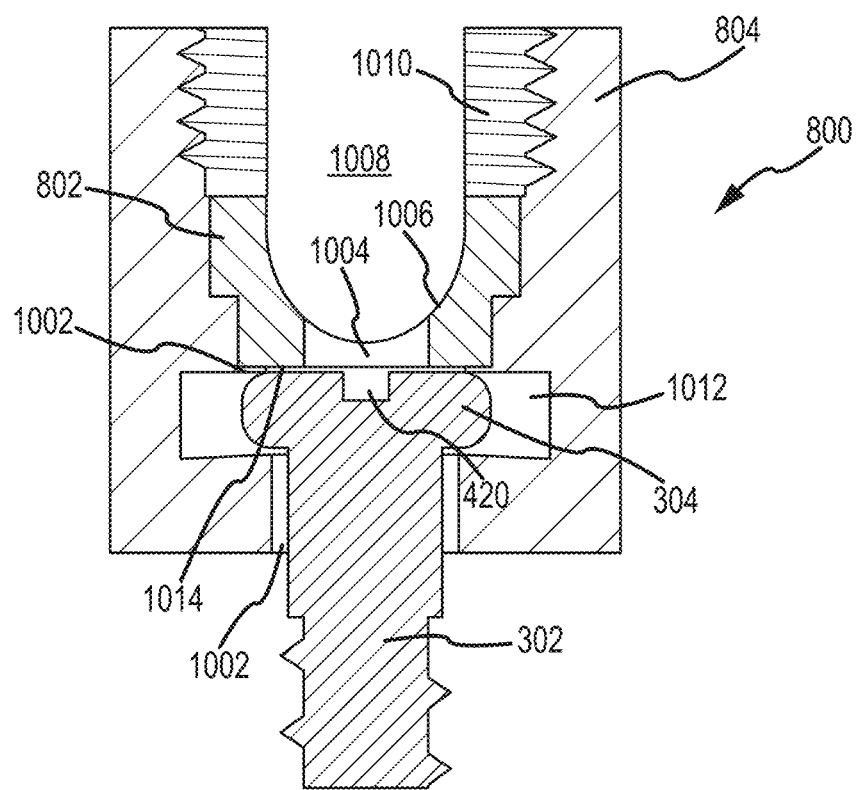
FIG. 10 is a cross-sectional view of a screw assembly that includes a snap-in lock.

FIG. 10 is a cross-sectional view of the screw assembly 800 in which the pedicle screw 302 is shown inserted through the lower cavity 1002 contained within the head socket 804. The snap-in lock 802 is shown snapped into place over the rounded screw head 304. An access bore 1004 is defined through the central axis of the snap-in lock 802 to provide access to a screw-tightening tool as described previously. The exposed surface 1006 of the snap-in lock 802 further defines the lower portion of an upper groove 1008. The upper portion of the upper groove 1008 is defined by the walls of the threaded cap receptacle 1010 of the head socket 804. A rod (not shown) may be situated within the upper groove 1008 and held in a fixed position by twisting the threaded head cap 312 into the threaded cap receptacle 1010. Two or more screw assemblies 800 may be linked together in the manner described previously for screw assemblies 300 and illustrated in FIG. 5.

The screw head 304 may slide along a curved groove 1012 contained within the head socket 802. The upper portion of the groove 1012 is defined by a curved lower surface 1014 of the snap-in lock 802. As described previously, the range of motion of any vertebrae stabilized by a dynamic spinal stabilization device comprising the screw assemblies 800 is governed by the dimensions and radius of curvature of the curved groove 1012 and screw head 304.

Any suitable materials may be used to produce the embodiments of the dynamic spinal stabilization devices, so long as the material possesses sufficient strength, durability, and biocompatibility to function in the context of orthopedic devices. Non-limiting examples of suitable materials for the construction of the dynamic spinal stabilization devices include titanium such as Ti6Al4V titanium, stainless steel, and any combination thereof.

c. Applications of Dynamic Spinal Stabilization Devices

The dynamic spinal stabilization devices may be used for the treatment of high grade spinal disorders such as spinal stenosis as well as spondylolisthesis. The devices may be used to stabilize spinal segments at any location along the spine, including but not limited to the cervical, thoracic, lumbar, and any combination thereof.

Figure 23:
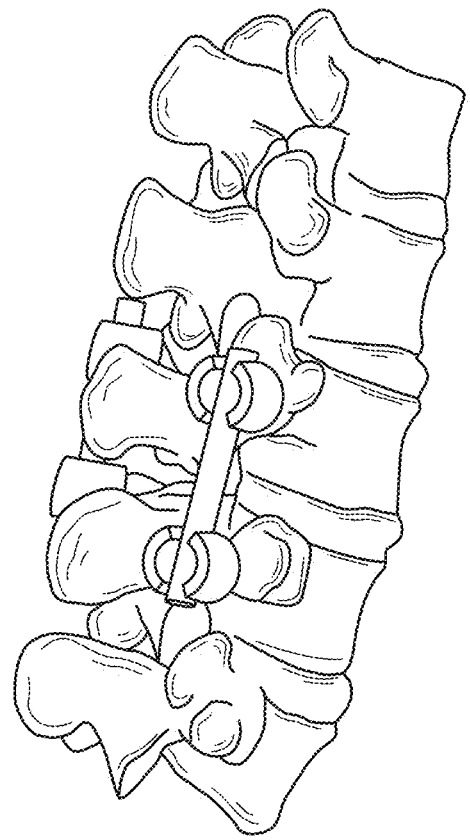
FIG. 23 is an image of a finite element model of a human spinal segment with a dynamic spinal stabilization implant installed.

Typically, the devices may include two sets of two or more connected screw assemblies that are linked together by a rod, as shown in FIG. 5. Each set of connected screw assemblies may be implanted on the spinous process on both the cranial and caudal vertebra of an affected motion segment such that one screw assembly is attached to the cranial vertebra and the other screw assembly is attached to the caudal vertebra. Two sets of connected screw assemblies may be implanted such that the sets are symmetrically spaced laterally to the left and right of the vertebra midline in order to provide enhanced lateral stabilization, as illustrated in FIG. 23.

Each pedicle screw head is free to slide inside of the head socket within a limited range of motion as described above to allow flexion-extension movement. In addition, each pedicle screw is free to rotate within the head socket to provide motion within a range limited by the connecting rods in lateral bending. Relatively little range of motion for lateral (side-to-side) movement of the pedicle screw head within the head socket is provided, resulting in additional stabilization of the spine during axial rotation.

i) Assembly of Screw Assemblies

Referring back to FIG. 4, each screw assembly 300 in one embodiment may be assembled preoperatively by inserting the round head 304 of the pedicle screw 302 into the curved groove 402 within the threaded lower cavity 414 of the head socket 310. The locking ring 314 may be threaded into the threaded lower cavity 414, with the neck 306 of the pedicle screw 302 situated within the slot 704 (shown in FIG. 7) of the locking ring 314 such that the threads of the pedicle screw 302 protrude downward from the head socket 310. The locking ring 314 may be tightened into place in order to retain the round head 304 within the curved groove 402.

In another embodiment, illustrated in FIG. 10, each screw assembly 800 may be assembled either preoperatively or during the surgical procedure by inserting the round head 304 of the pedicle screw 302 through the lower cavity 1002 of the head socket 804 such that the threads of the pedicle screw 302 protrude downward from the head socket 804. The snap-in lock 802 may then be snapped into place over the screw head 304.

ii) Fixation of Screw Assemblies

The assembled screw assemblies may be installed in place in the pedicle of a vertebra that is situated cranially or caudally to an affected motion segment. Referring again to FIG. 4, the screw assembly 300 may be installed by inserting a screw-tightening tool through the access bore 408, mechanically engaging the fitting 420 in the screw head 304 with the screw-tightening tool, and applying torque to the screw 302 in order to tighten the pedicle screw 302 to an appropriate depth. In an embodiment, the pedicle screw 302 may include a raised lip 308 to mechanically limit the insertion of the pedicle screw 302 to the appropriate depth.

Any known screw-tightening tool appropriate for orthopedic surgical applications may be used, so long as the screw-tightening tool is matched to the fitting 420. Non-limiting examples of fittings 420 that are appropriate for use in the screw assembly 300 include slot fittings, Phillips fittings, hexagonal fittings, and the like.

Referring to FIG. 10, in another embodiment, the screw assembly 800 may be installed by inserting a screw-tightening tool through the access bore 1004 in the snap-in lock 802, mechanically engaging the fitting 420 in the screw head 304 with the screw-tightening tool, and applying torque to the screw 302 in order to tighten the pedicle screw 302 to the appropriate depth.

ii) Linking of Screw Assemblies

Referring to FIG. 5, the installed screw assemblies 300A and 300B may be linked together using a rigid rod 502. For example, a first end of a rod 504 may be situated within the upper groove of a head socket 310A of the installed screw assembly 300A on the vertebra that is cranial to an affected motion segment. Similarly, the second end of the rod 506 may be situated within the upper groove of a socket head 310B of the screw assembly 300B that is installed on a vertebra that is caudal to the affected motion segment. The rod 506 may then be held in a fixed position by twisting the threaded head caps 312A and 312B into the threaded cap receptacles of the head sockets 310A and 310B, respectively. Sufficient torque may be applied to the head caps 312A and 312B so as to hold the rod in a fixed force-fit engagement.

EXAMPLES

The following examples illustrate various embodiments of the invention.

Example 1

Estimated Effects of Pedicle Screw and Head Socket Geometry on the Range of Motion of a Stabilized Vertebral Segment To assess the impact of the geometry of a pedicle screw/head socket assembly on the range of motion of a vertebrae stabilized using an implant that incorporates the pedicle screw/head socket assembly, the following experiments were conducted. A mathematical model of a pedicle screw and head socket motion within the slot was developed using MathCad (PTC, Needham, Mass.). The head socket's slot width, radius of curvature of the inner slot surface, and the screw head width were varied to determine the effects of changes in these dimensions to the center of rotation and range of motion of a vertebral segment stabilized using an implant. In this experiment, a design goal for the pedicle screw assembly was to provide approximately 7° of movement in flexion and 7° in extension of the stabilized vertebral segment, corresponding to a total of 14° of movement for combined flexion and extension for a vertebral segment stabilized using a complete bilateral stabilization system.

The degree of sliding motion of the pedicle screw head within the head socket was evaluated by adjusting the slot width until the desired angle of the pedicle screw was achieved. The inner slot surface was given a constant radius of curvature, resulting in the projection of the theoretical center of rotation of the screw/head socket assembly to a distance equal to the radius of curvature of the inner slot surface. A larger radius of curvature of the inner slot surface was determined to project the center of rotation a greater distance, and a wider head socket slot allowed greater range of motion of a stabilized vertebral segment.

Based in these initial results, a radius of curvature of 40 millimeters for the inner slot surface was found to project the center of rotation of a stabilized vertebral segment to a location that was coincident with the intervertebral disc.

Figure 11:
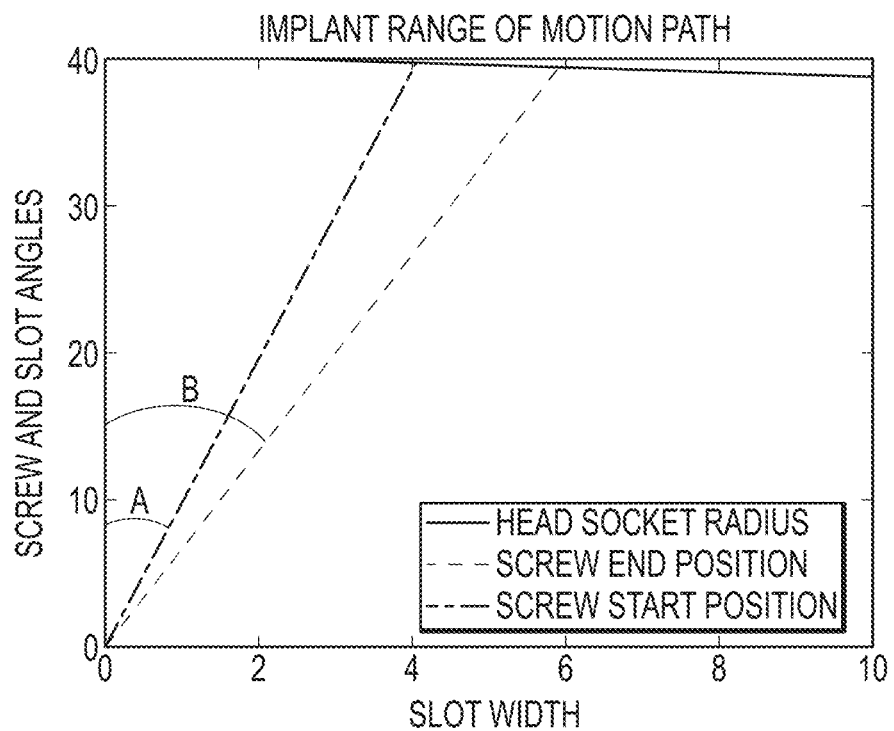
FIG. 11 is a graph showing the estimated screw and slot angles as a function of slot width of a pedicle screw assembly.

The potential range of movement of the screw within the socket head was then evaluated using the MathCad model using variations in the head socket's slot width and the pedicle screw head width. A larger size difference in these parts allowed a wider range of movement. The total movement was calculated by taking the difference in the angles of the slot width and screw width, or the difference in angle B and angle A, as shown in FIG. 11. The screw head width was assumed to be the starting position of the movement and the slot width was assumed to be the end position. Since the slot was axially symmetrical, the calculation was done on one-half of the screw movement.

Figure 12:
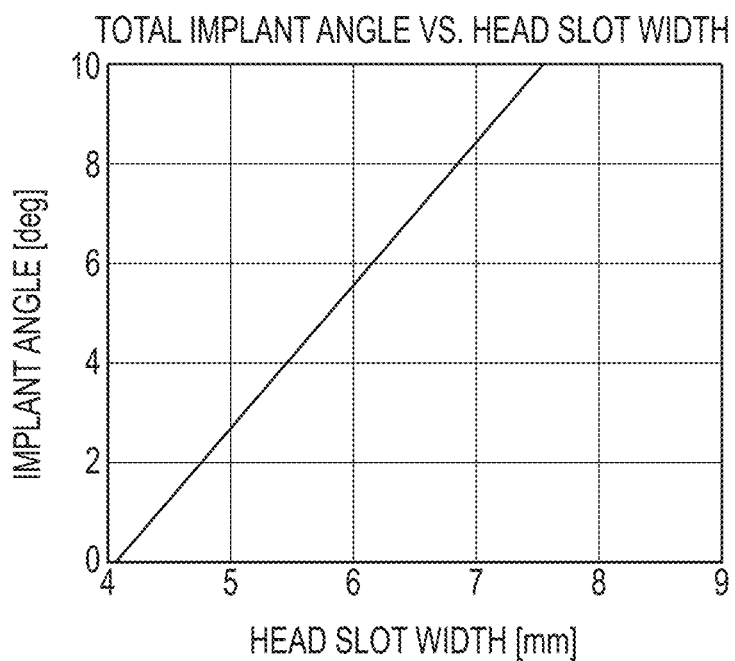
FIG. 12 is a graph showing the estimated total implant angle as a function of the head slot width of a pedicle screw assembly.

The range of motion of the implant as a function of slot width was also calculated in MathCad. As seen in FIG. 12, the range of movement, as represented by the maximum implant angle, increases as the head slot width increases. Based on these MathCad estimates, the slot width needed to achieve 7.0° of rotation was approximately 6.5 mm. However, due to size limitations on the implant, a 6.0 mm slot width with a screw head diameter of 4 mm was evaluated. This combination of slot width and screw head diameter resulted in a head socket width of 16.5 mm and an estimated implant range of movement through an angle of 5.56°, which fulfilled both the functional and implant size constraints imposed in this experiment. In order to prevent binding of the screw head and slot surface and to increase the range of Motion of the implant to a full 7°, a gap of 0.5 mm between the screw head and slot surface was incorporated into the implant design resulting from these experiments.

The results of these experiments provided a preliminary evaluation of the potential range of movement for a variety of different implant designs. In addition, the results of this experiment determined the sensitivity of the range of movement and center of rotation of a stabilized vertebral segment to variations in the dimensions of the screw head and head socket used in the construction of an implant.

Example 2

Figure 13:
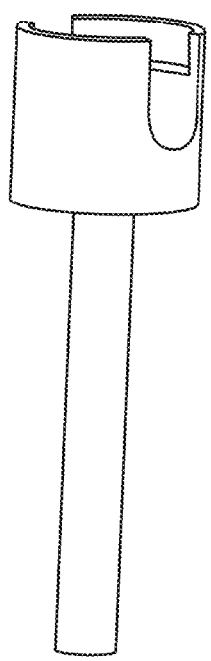
FIG. 13 is an image of a finite element model of a screw assembly.

Theoretical Assessment of the Range of Motion of a Stabilized Vertebral Segment Using Finite Element Modeling Computational finite element modeling of the pedicle screw/head socket assembly using ABAQUS (Version 6.8, Simulia, Providence, R.I.) was performed in order to verify the device's motion characteristics. Initially, a half model consisting only of the pedicle screw, lock ring, and head socket was used to evaluate the implant's motion in order to reduce computational cost. The three parts were meshed using 7,768 eight node linear brick hexahedral elements for the head/lock ring assembly and 13,256 hexahedral elements for the pedicle screw. The meshed model used in this experiment is shown in FIG. 13.

An encastre boundary condition was applied via a kinematic distributing tie to the top surface of the head piece to hold it in place while a 7 Nm moment was applied to the pedicle screw using a second distributing tie constraint. Material properties of Ti6Al4V were applied to all parts, and contact interactions were applied between the pedicle screw and head pieces.

The pedicle screw head was modeled with a corner radius of 1.0 mm applied to the upper and lower edges in order to promote smoother motion and to for a total rotation angle of 7.0° within the slot of the head socket.

Figure 14:
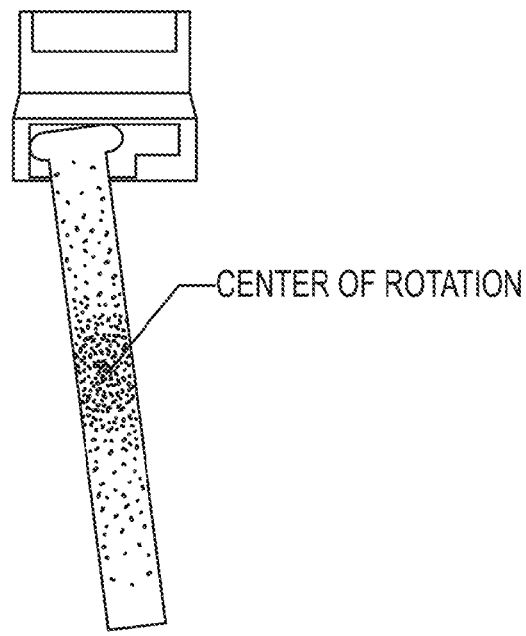
FIG. 14 is a cut-away view of a finite element model of a screw assembly showing the estimated range of motion and center of rotation of the screw.

An image of the finite element model showing the maximum movement and center of rotation of the pedicle screw within the head socket is shown in FIG. 14. The results of this initial finite element experiment indicated that the implant half-model reached a total rotation of 7.1° and had a center of rotation located 22.5 mm away from the screw head. The range of motion and center of rotation location were consistent with the desired properties for a dynamic stabilization implant.

Figure 15:
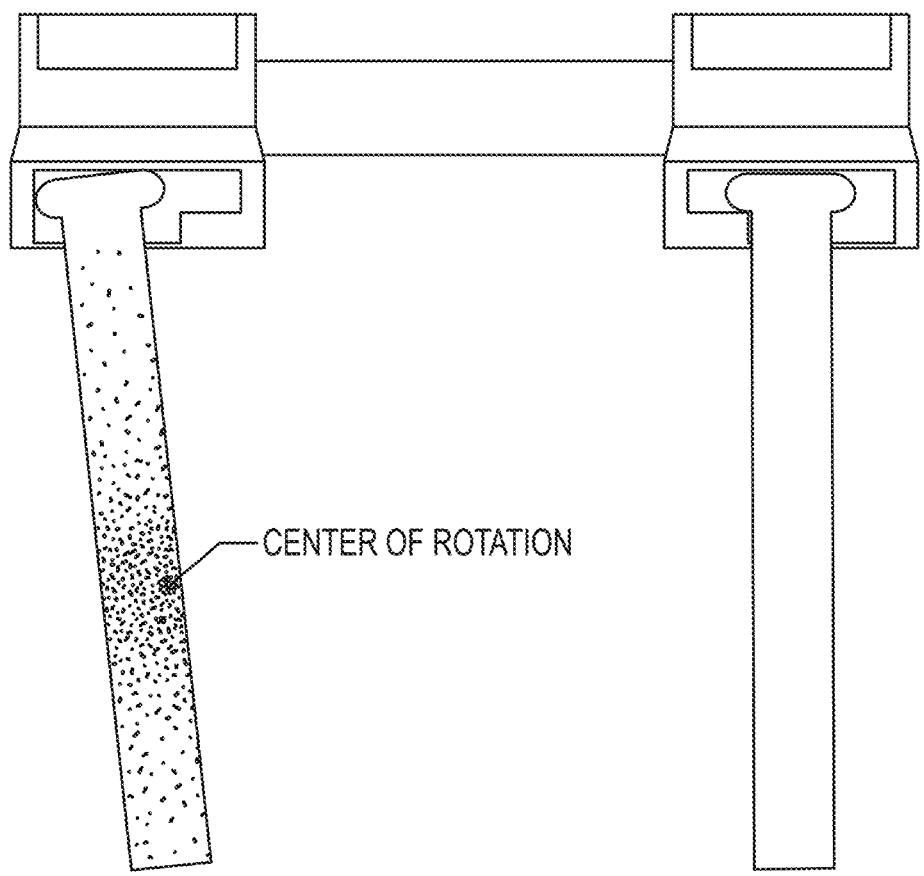
FIG. 15 is a cut-away view of a finite-element model of a half-implant assembly showing the estimated range of motion and center of rotation of the half-implant.

Using an expanded finite elements model, shown in FIG. 15, the range of motion and center of rotation of a full implant was evaluated in similar fashion to the half-model. Two pedicle screw assemblies were connected with a 6.35 mm rod using additional tie constraints. A 7 Nm moment was applied to one pedicle screw with a kinematic distributing tie constraint, while the second pedicle screw was fixed in place with an encastre boundary condition. The results of this evaluation were consistent with the initial results from the single pedicle screw study.

Appropriate mesh refinement for all models was confirmed via a convergence study. Three meshes of the same implant model were created with 5638, 21,024, and 50,707 hexahedral elements respectively. The implant model's rotation during flexion was calculated for each model until minimal change occurred between the different mesh densities.

Figure 16:
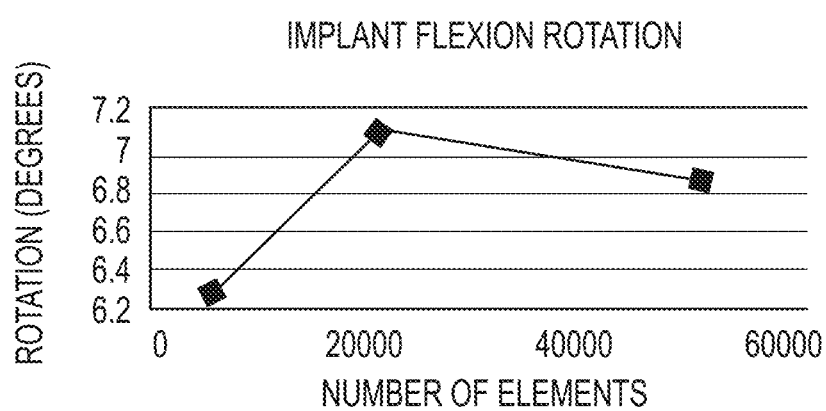
FIG. 16 is a graph summarizing the results of a convergence study showing the rotation of a half-implant assembly estimated using finite element models with three different mesh resolutions.

The results of the convergence study are summarized in FIG. 16. The low density mesh model rotation was 6.3 degrees, the medium density model rotated 7.08 degrees, and the high density model rotated 6.85 degrees during flexion. There was a difference of 3.3% between the medium and high density models, indicating good convergence of the results of the finite element models used in these experiments.

The results of this experiment confirmed the preliminary range of motion estimates for the implant evaluated in Example 1, and further refined the design of the implant to include a corner radius of 1.0 mm on the upper and lower edges of the pedicle screw head to permit the movement of the implant through the full desired rotation range of 7°.

Example 3

Figure 17:
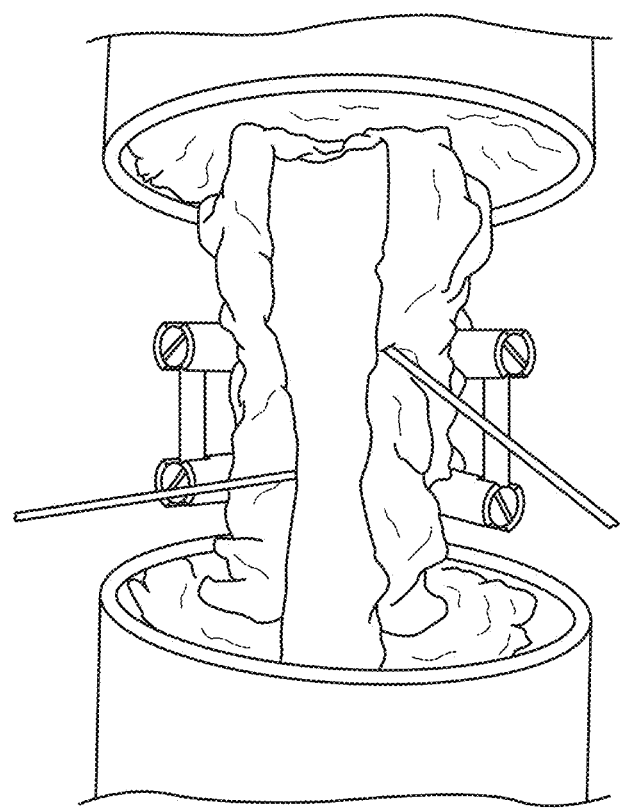
FIG. 17 is a photograph showing a prototype dynamic spinal stabilization device installed at the L3-L4 level of a cadaver spine preparation.

Experimental Assessment of the Motion of Stabilized Vertebral Segments Using Radiographs of Cadaver Spine Preparations To empirically assess the range of motion and center of rotation of a vertebral segment stabilized using a prototype implant similar in design to the implants evaluated in Example 1 and Example 2, the following experiments were conducted. Human cadaver spines (n=2) were used to experimentally validate the center of rotation and intersegmental range of motion of the implant prototype. Four different spinal preparations were modeled in the study: intact, injured, fused, and implanted with the prototype dynamic stabilization implant. A photograph of the cadaver spine preparation is shown in FIG. 17.

The four different spinal preparations were produced sequentially using step-wise transformations of the intact cadaver spines. The facet joints of the L3 and L4 vertebrae were removed using bone rougeurs in order to produce the injured spine model. For the fused spine model, fusion pedicle screws were implanted to the injured spine model, a 6.35 mm titanium rod was connected to the pedicle screws, and the cap screws of the fusion pedicle screws were tightened with a 4 Nm torque. For the implanted model, the fusion pedicle screws were removed and replaced with the prototype implant pedicle screws. The pedicle screws of the prototype implant were connected with the same titanium rod and held in place by the cap screws.

Lateral radiographs of the four spine models in the neutral, maximum flexion, and maximum extension states for all four test configurations where obtained and the center of rotation for each extension state was calculated from the radiograph images. The calculated center of rotation points were normalized and plotted on a single radiograph for the four extension states, as shown FIG. 18.

Figure 18:
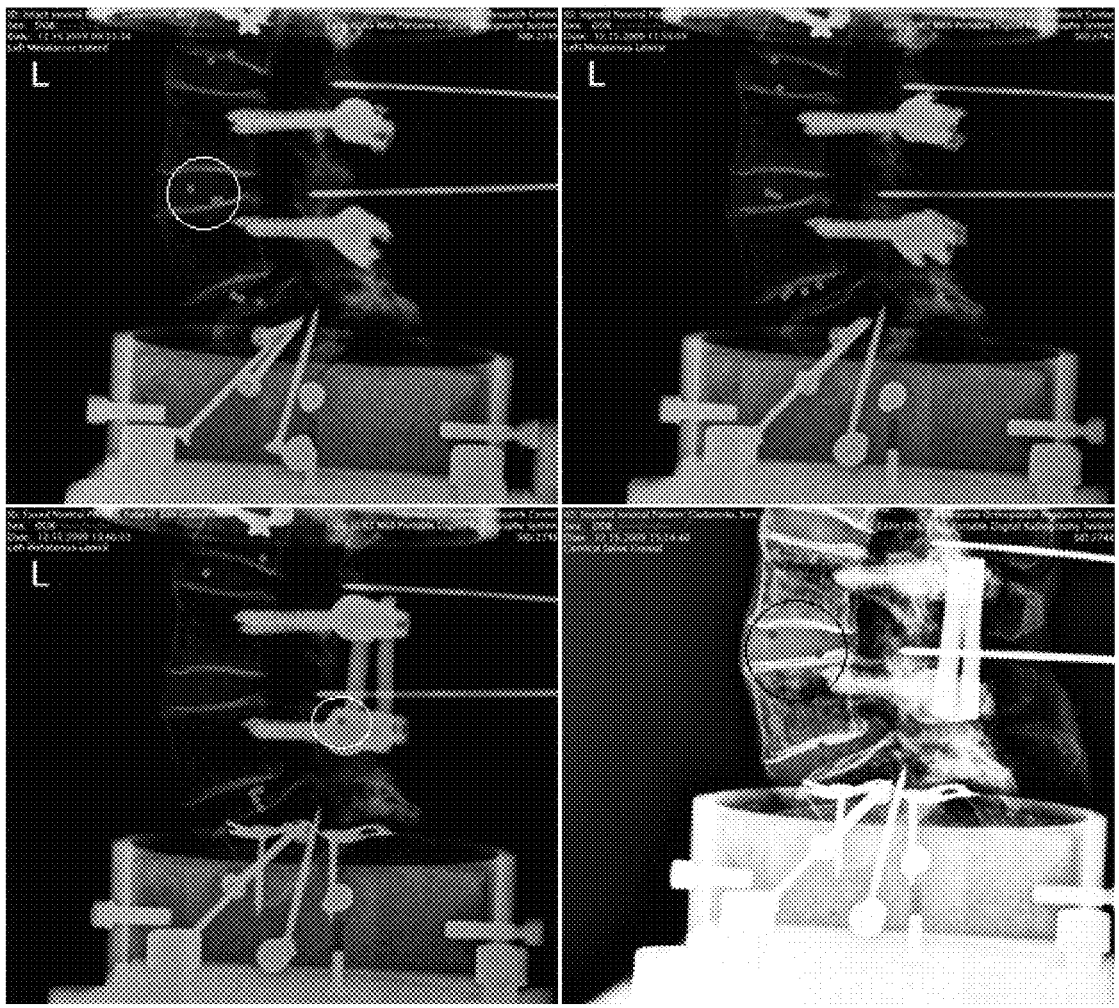
FIG. 18 includes four radiograph images showing the axis of rotation of four cadaver spine preparations: intact (upper left), injured (upper right), fused (lower left), and stabilized with a dynamic spine stabilization implant (lower right).

The centers of rotation (CORs) for the intact spine were closely clustered in the center of the intervertebral disc for all three of the spine's motion segments as seen in the top left image of FIG. 18. Removing the facet joints had little influence on the centers of rotation in the injured spine as seen in the top right image of FIG. 18. Adding a fusion device increased the scatter of COR points in the segment cranial to the affected level as seen in the bottom left image of FIG. 18. The COR at the fused level moved in a posterior direction toward the caudal pedicle screw. In one trial the COR failed to move due to loosening of the screw. Results of the dynamic stabilization implant, as shown in the bottom right image of FIG. 18, indicated COR restoration to positions inside the intervertebral disc and caudal vertebral body.

The results of these experiments confirmed that the dynamic stabilization implant effectively projected the motion segment center of rotation back to inside of the intervertebral disc and caudal vertebral body.

Example 4

Experimental Assessment of the Motion of Stabilized Vertebral Segments Using 3-Dimensional Motion Analysis of Spine Preparations To further assess the range of motion and center of rotation of a vertebral segment stabilized using a dynamic stabilization implant similar in design to the implants evaluated in Example 1 and Example 2, the following experiments were conducted.

Using the cadaver spinal preparations described in Example 3, the spinal intersegmental kinematics were evaluated in addition to testing the instantaneous axis of rotation. A three-camera motion analysis system (Motion Analysis Corp, Santa Rosa, Calif.) was used to analyze the motion of reflective markers placed on the vertebrae. Three non-collinear markers, referred to as a triad, were attached to each vertebra with Kirschner wires. The movement of each triad during flexion and extension was recorded in Cartesian coordinates and transformed into Euler angles using Matlab, a data analysis program (The Mathworks, Inc., Natick, Mass.). The calculated Euler angles quantified the relative intersegmental rotation of each vertebra.

The four spine models described in Example 3 were tested in flexion and extension using methods similar to those described in Example 3. Pure moments of ±7.5 Nm were applied in flexion-extension, bilateral bending, and biaxial rotation for each spine model. Nine cycles were completed for each motion in order to fully pre-condition the specimen and eliminate any viscoelastic behavior. Rotation data was obtained and analyzed from the final rotation cycle of each motion.

Figure 19:
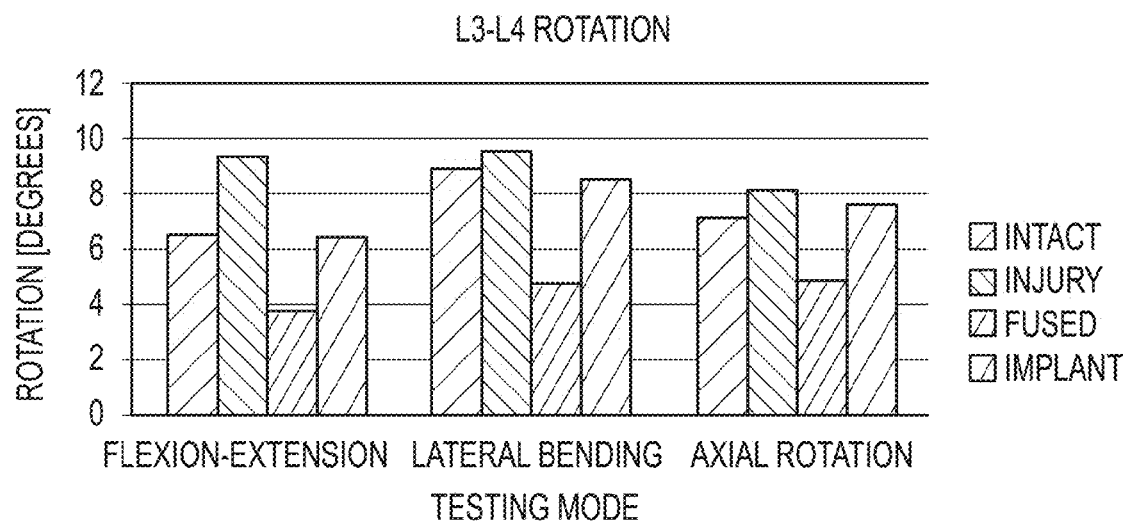
FIG. 19 is a graph showing the rotation angles estimated using 3-dimensional motion analysis of the videotaped movements of four cadaver spine preparations: intact, injured, fused, and stabilized with a dynamic spine stabilization implant.
Figure 20:
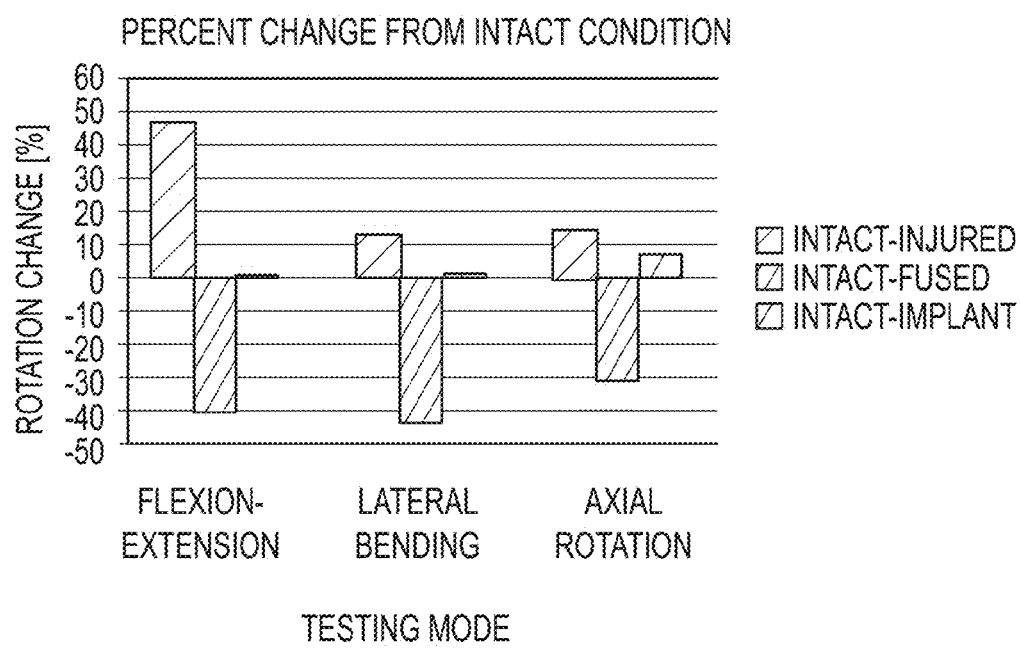
FIG. 20 is a graph showing the rotation angles of experimental cadaver spine preparations relative to the intact cadaver spine preparation estimated using 3-dimensional motion analysis of the videotaped movements of the cadaver spine preparations.

The results of the three-dimensional motion analysis of the vertebral kinematic data are summarized in FIG. 19. The changes in rotation as a percentage of the intact spinal model's rotation for each direction of rotation are presented in FIG. 20. All rotations were assessed at the L3 L4 level, which corresponded to the level at which the injury and subsequent stabilization using fusion and the prototype implant was situated in the spine models. The intact spine model experienced a rotation of 6.42° in flexion-extension. The injured spine model rotated 9.39° in flexion-extension, corresponding to an increase of 2.97° (46.26%) relative to the intact spine model. Installing the fusion rod at the L3 L4 level decreased rotation to 3.79°, corresponding to a decrease of 5.6° (59.64%) relative to the injured model and a decrease of 2.63° (40.97%) relative to the intact model. The prototype implant restored the flexion-extension rotation to 6.45°, or within 0.03° (0.47%) of the intact condition.

Similar results were observed for bilateral bending; the implant prototype restored intersegmental rotation to 8.58°, a difference of 0.08° (0.82%) from the intact scenario. In axial rotation, the implant spinal model rotated 7.65°, which was within 0.50° (6.99%) of the intact spine's axial rotation. A summary of the rotation angles of the implant spinal model compared to the intact spinal model are summarized in Table 1.

TABLE 1

Rotation Angles and Changes Relative to Intact Spinal Model from 3-D Motion Analysis

| Spinal Model | Rotation Angle (degrees) | | | | | |
|---|---|---|---|---|---|---|
| | Flexion-Extension | | Bilateral Bending | | Axial Rotation | |
| | Angle | % diff. | Angle | % diff. | Angle | % diff. |
| Intact | 6.42 | — | 8.50 | — | 7.15 | — |
| Implant | 6.45 | 0.47% | 8.58 | 0.82% | 7.65 | 6.99% |

The results of this experiment verified that the stabilization of an injured spinal segment using a dynamic stabilization implant similar in design to the implant described in Examples 1 and 2 resulted in intersegmental rotation angles that were comparable to the intact spine model. By contrast, stabilization by spinal fusion resulted in rotation angles that were significantly lower than the corresponding rotations of the intact spinal model.

Example 5

Finite-Element Model Assessment of the Range of Motion of a Vertebral Segment Stabilized Using a Second-Generation Pedicle Screw/Head Socket Design To assess the range of motion of a refined dynamic stabilization implant design similar to that illustrated in FIG. 8, the following experiments were conducted. Computational finite element modeling of the implant was performed using ABAQUS (Version 6.8, Simulia, Providence, R.I.). A pedicle screw, head, and snap were modeled using 38,220, 45,252, and 3,350 8-node hexahedral elements respectively. Ti6Al4V material properties with a coefficient of friction of 0.3 were assigned to all parts. The required mesh density was confirmed via a convergence study using methods similar to those described in Example 2.

Figure 21:
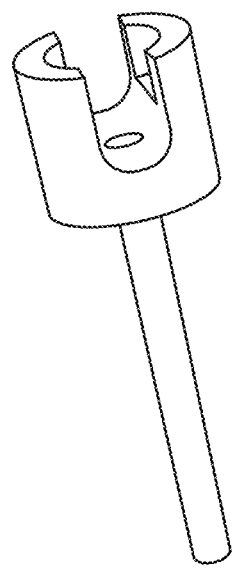
FIG. 21 is an image of a finite element model of a screw assembly that includes a snap-in lock.

A single pedicle screw assembly, illustrated in FIG. 21, was modeled to reduce computational time. Identical boundary conditions to those described in Example 2 were imposed on the model. A 5.5 Nm moment was applied to the pedicle screw shaft to induce flexion/extension movements of the pedicle screw within the head socket.

Figure 22:
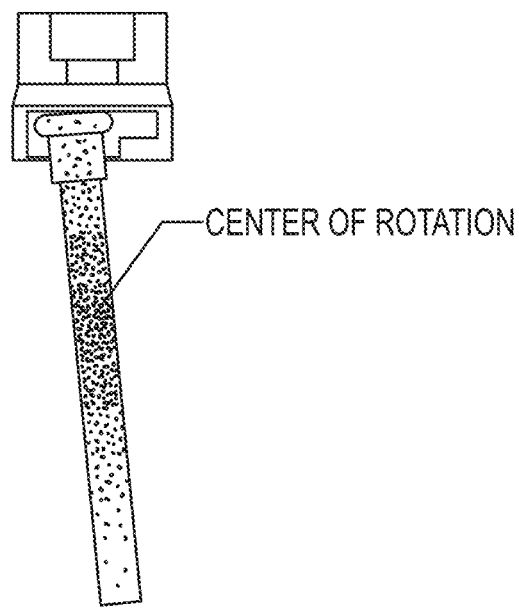
FIG. 22 is a cut-away view of a finite element model of a screw assembly that includes a snap-in lock showing the estimated range of motion and center of rotation of the screw.

FIG. 22 illustrates the results of the finite elements assessment. The center of rotation was displaced about 20.2 mm from the pedicle screw head, which was nearly identical to the corresponding center of rotation of the previous implant design analyzed in Example 2. The total pedicle screw rotation angle determined by this finite element model was 8.5°, which was slightly higher comparable to the rotation angle of 7.1° of the previous implant design analyzed in Example 2.

A previously validated L1-L5 lumbar spine finite element model was used to further study implant motion during spinal flexion. This direction of spinal rotation was selected for analysis because the characteristic sliding motion of the dynamic stabilization implant had the greatest impact on spinal rotation in that direction. The facet joints at the L3/L4 level were removed from the finite element model and a finite element model of the implant was incorporated using methods similar to those described in Example 2. The finite element model of the spinal segment with the dynamic stabilization implant is illustrated in FIG. 23. A 7.5 Nm flexion moment was applied to the superior endplate of the L1 vertebra of the model, and the inferior endplate of the L5 vertebra of the model was fixed with an encastre boundary condition.

Figure 24:
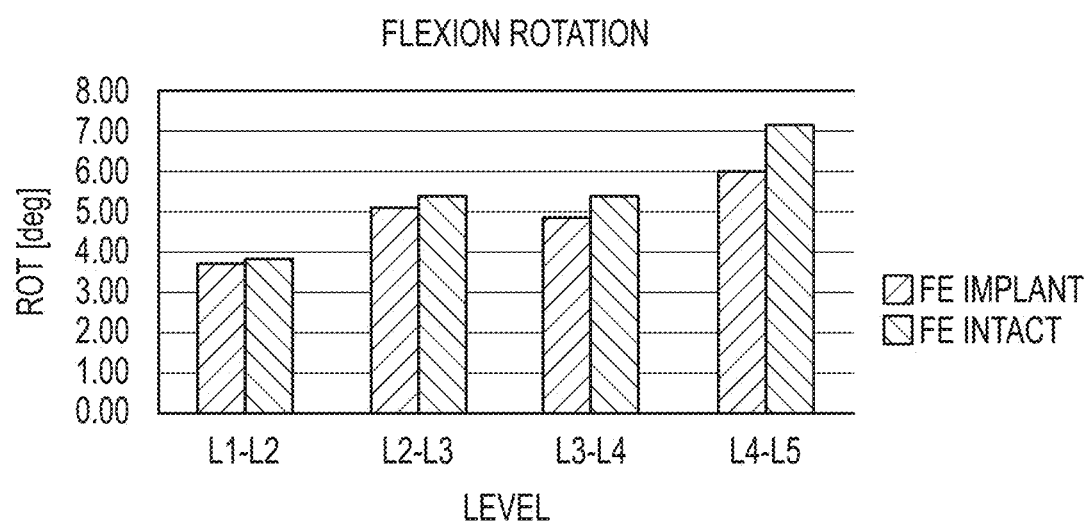
FIG. 24 is a graph comparing the relative rotation of 4 different spinal segment levels estimated using finite element models during spinal flexion for an intact spine and an injured spine stabilized with a dynamic spinal stabilization implant.
Figure 25:
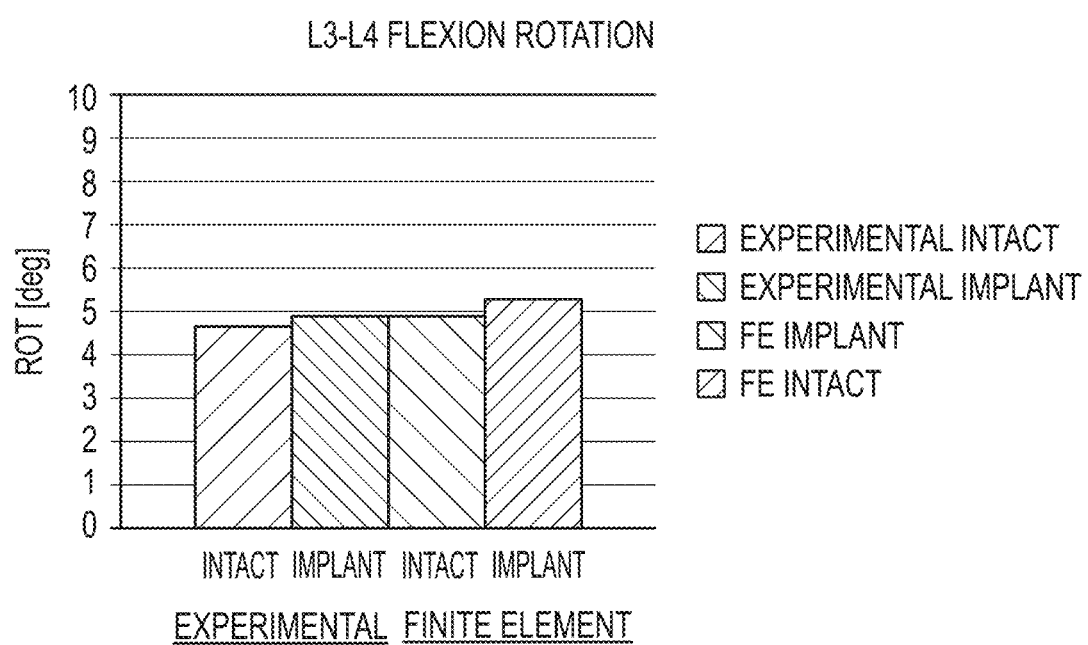
FIG. 25 is a graph comparing the relative rotation of the L3-L4 spinal segment during spinal flexion for an intact spine and an injured spine stabilized with a dynamic spinal stabilization implant, comparing experimental measurements using a cadaver spinal preparation and a finite element model.

The rotations during flexion of the finite element model of the intact spine and injured spine stabilized with the implant are summarized in FIG. 24. Little change in motion occurred at the L1-L2 and the L2-L3 levels due to the addition of the implant. A 0.4° (7.6%) decrease in rotation at the L3-L4 (implanted) level and a 1.1° (15.6%) decrease in rotation at the L4-L5 level occurred in the model due to implant installation. As summarized in FIG. 25, the results of the finite element study of this experiment are in close agreement with the experimental observations of flexion of the cadaver spine models described in Example 4. All rotations for the implanted segments of this experiment fell within 0.6° of the corresponding experimental results described in Example 4.

The L1-L5 lumbar spine finite element model was also used to determine the flexion of the intact model and the injured/implanted model as a function of applied flexion moment. The flexion rotation as a function of flexion moment for the L1-L2 level, L2-L3 level, L3-L4 level, and L4-L5 level are presented in FIGS. 26A-D, respectively. In general, the implant does not alter the motion pattern of any motion segment in flexion despite small changes in magnitude at the L3-L4 and L4-L5 levels. In addition, the screw head experienced smooth sliding within the head socket, and no implant locking or binding was observed during this analysis.

The results of this experiment confirmed that the implant did not alter the natural loading pattern of the lumbar spine in flexion.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The invention claimed is:

1. A screw assembly for use in a dynamic spinal stabilization device, the screw assembly comprising:
   a head socket comprising a lower face containing a slot extending diametrically across a central portion of the lower face, and further extending upward between the lower face and a curved lower cavity surface of an upper cavity of the head socket;
   a lock comprising an exposed upper lock surface and a curved lower lock surface, wherein the lock is to be placed in the head socket over the curved lower cavity surface to form an internal curved groove between the curved lower lock surface and the curved lower cavity surface; and
   a pedicle screw comprising a screw head to be retained within the internal curved groove and a screw neck to extend downward from the screw head through the slot;
   wherein, when the screw head is retained within the internal curved groove, the screw head freely slides along the internal curved groove along a range of movement limited by a length of the slot, and a center of rotation of the pedicle screw is situated at a distance downward from the screw head that is equal to a radius of curvature of the internal curved groove.

2. The screw assembly of claim 1, further comprising an exposed upper groove extending diametrically across the upper cavity, the exposed upper lock surface forming at least part of a curved bottom portion of the exposed upper groove.

3. The screw assembly of claim 2, wherein the head socket further comprising a lower portion comprising the lower face, the head socket further comprising at least two walls extending upward from a base portion, the two walls forming at least an uppermost portion of the exposed upper groove.

4. The screw assembly of claim 2, wherein an uppermost portion of the exposed upper groove comprising a thread structure to receive a threaded head cap.

5. The screw assembly of claim 2, wherein the exposed upper groove extends horizontally and parallel to the slot.

6. The screw assembly of claim 1, wherein the lock comprising a snap-in lock to be locked into place in the head socket over the curved lower cavity surface.

7. The screw assembly of claim 1, wherein the lock comprising at least one tab to be inserted into an indentation of the upper cavity when the lock is placed in the head socket.

8. The screw assembly of claim 1, wherein the lock defining an access bore exposing at least a portion of a top surface of the screw head when the lock is placed in the head socket and the screw head is retained within the internal curved groove.

9. The screw assembly of claim 1, wherein the internal curved groove extending along a direction defined by the slot.

10. The screw assembly of claim 1, wherein the screw head comprising a rounded screw head.

11. The screw assembly of claim 1, wherein the pedicle screw further comprising a lip structure below the screw neck, the lip structure extending below the lower face of the head socket when the screw head is retained within the internal curved groove.

12. The screw assembly of claim 11, wherein the pedicle screw further comprising a threaded structure extending downward from the lip structure, the threaded structure to be implanted into a vertebra.

13. The screw assembly of claim 1, wherein the length of the slot limits a rotation of the pedicle screw about the center of rotation of the pedicle screw to a range of movement that is consistent with a physiologically normal rotation of a spinal segment to be stabilized using the dynamic spinal stabilization device.

14. The screw assembly of claim 13, wherein the range of movement of the pedicle screw is limited to less than about ±10 degrees from a central axis of the head socket.

15. The screw assembly of claim 14, wherein the range of movement of the pedicle screw is limited to less than about ±7 degrees from a central axis of the head socket.

16. The screw assembly of claim 1, wherein the center of rotation of the pedicle screw is situated within a region chosen from: a body of a vertebra in which the pedicle screw is configured to be implanted, and a disk adjacent to a vertebra in which the pedicle screw is configured to be implanted.

17. The screw assembly of claim 1, wherein the head socket comprises a cylindrical head socket.

18. A method of assembling a screw assembly, the method comprising:
- inserting a bottom portion of a pedicle screw downwardly through a slot in a lower face of a head socket until a screw neck extending downward from a screw head of the pedicle screw extends through the slot, the slot extending diametrically across a central portion of the lower face, the slot further extending upward between the lower face and a curved lower cavity surface of an upper cavity of the head socket; and
- placing a lock comprising an exposed upper lock surface and a curved lower lock surface in the head socket over the curved lower cavity surface to form an internal curved groove between the curved lower lock surface and the curved lower cavity surface, the screw head of the pedicle screw to be retained within the internal curved groove;

wherein, when the screw head is retained within the internal curved groove, the screw head freely slides along the internal curved groove along a range of movement limited by a length of the slot, and a center of rotation of the pedicle screw is situated at a distance downward from the screw head that is equal to a radius of curvature of the internal curved groove.

19. The method of claim 18, further comprising:
- inserting, after the placing of the lock, an end of a screw-tightening tool through an access bore defined by the lock, the access bore exposing at least a portion of a top surface of the screw head to engage the end of the screw-tightening tool with the top surface of the screw head; and
- driving, using the screw-tightening tool, a threaded structure of the pedicle screw extending downward from the screw neck of the pedicle screw into a vertebra.

20. The method of claim 19, wherein the driving continuing until a lip structure of the pedicle screw between the screw neck and the threaded structure contacts the vertebra.

21. The method of claim 19, further comprising:
- placing a connecting rod within and along an exposed upper groove extending diametrically across the upper cavity, the exposed upper lock surface forming at least part of a curved bottom portion of the exposed upper groove; and
- twisting a threaded head cap into a thread structure of an uppermost portion of the exposed upper groove to secure the connecting rod to the head socket.

* * * * *